(12) United States Patent
Hewitt et al.

(10) Patent No.: US 11,920,127 B2
(45) Date of Patent: Mar. 5, 2024

(54) FORENSIC RECOVERY OF IDENTIFICATION FROM SHELL CASINGS

(71) Applicant: Signature Science, LLC, Austin, TX (US)

(72) Inventors: F. Curtis Hewitt, Austin, TX (US); Tierney Sugrue, Clementon, NJ (US); Benjamin Ludolph, Round Rock, TX (US); Kathleen Schulte, Cedar Park, TX (US)

(73) Assignee: Signature Science, LLC, Austin, TX (US)

( * ) Notice: Subject to any disclaimer, the term of this patent is extended or adjusted under 35 U.S.C. 154(b) by 360 days.

(21) Appl. No.: 17/112,947

(22) Filed: Dec. 4, 2020

(65) Prior Publication Data

US 2021/0171933 A1 Jun. 10, 2021

Related U.S. Application Data

(60) Provisional application No. 62/943,544, filed on Dec. 4, 2019.

(51) Int. Cl.
*C12N 15/10* (2006.01)

(52) U.S. Cl.
CPC .................. *C12N 15/1013* (2013.01)

(58) Field of Classification Search
CPC .............. C12N 15/1013; C12Q 1/6806; C12Q 2523/32; C12Q 2563/149; C12Q 2563/143
See application file for complete search history.

(56) References Cited

PUBLICATIONS

Dieltjes et al. A sensitive method to extract DNA from biological traces present on ammunition for the purposes of genetic profiling. Int. J. Legal Med. (2011) 125:597-602. (Year: 2011).*

Horsman-Hall et al. Development of STR profiles from firearms and fired cartridge cases. Forensic Science International: Genetics (2009) 3:242-250. (Year: 2009).*

Montpetit et al. An optimized procedure for obtaining DNA from fired and unfired ammunition. Forensic Science International: Genetics (2015) 17:70-74. (Year: 2015).*

\* cited by examiner

*Primary Examiner* — David C Thomas
(74) *Attorney, Agent, or Firm* — John A. Fortkort; Fortkort & Houston PC

(57) ABSTRACT

Non-destructive methods and devices are disclosed herein for overcoming the limitations associated with analyzing shell casings and other cylindrical items for biomolecular and fingerprint extraction and analysis. In a preferred embodiment of these methodologies and devices, the open end of a spent shell casing (or like object) is plugged with a handle. This approach reduces the risk of sample contamination by gunpowder residue, while also providing a convenient means for handling the shell casing that reduces the risk of contamination or sample loss. Spin baskets (or extraction tubes) are provided which may be customized to different shell casing diameters, thereby substantially reducing the volume of extraction buffer required for sample collection and enable ease of centrifugation. A strong surfactant is preferably utilized during collection, which may reduce the amount of time needed for collection to just minutes. The surfactant is preferably of a type that draws on the extracellular nature of DNA in the sample in such a way as to almost instantaneously pull it into solution upon exposure to the buffer. The full buffer volume is then rapidly collected through the spin basket for DNA purification. Additionally, the use of magnetic beads to rapidly separate DNA from metal ions and other inhibitory agents is a primary advancement of the methods. The systems and methodologies disclosed herein offer a possible paradigm shift for forensic laboratories as they analyze challenging types of casework evidence. In particular, these systems and methodologies may be utilized to improve the preservation, recovery and analysis of DNA, proteins, other forensically-relevant biomolecules, chemical, radiological, nuclear, or explosive residues, and fingerprints collected from shell casings or other like samples.

23 Claims, 3 Drawing Sheets

FORENSIC RECOVERY OF IDENTIFICATION FROM SHELL CASINGS

CROSS-REFERENCE TO RELATED APPLICATIONS

The present application claims the benefit of priority from U.S. Provisional Application No. 62/943,544, filed on Dec. 4, 2019, which has the same title and the same inventors, and which is incorporated herein by reference in its entirety.

FIELD OF THE DISCLOSURE

The present disclosure relates generally to forensic methods, and more particularly to the non-destructive methods for performing forensic analysis of fingerprint structure and biomolecules from shell casings or other cylindrical evidentiary samples.

BACKGROUND OF THE DISCLOSURE

Brass shell casings represent a particularly challenging class of forensic casework samples. The relatively small surface area provides little opportunity for DNA transfer. Shell casings may also be touched by multiple individuals prior to loading and firing, leading to mixtures of trace material. Firing produces intense heat that may damage DNA deposited on the shell. DNA may be further compromised by the presence of metal ions from the brass surface (i.e., copper) that produce strand breaks, degrading the DNA into fragments too short for polymerase chain reaction (PCR).

Sample collection from shell casings typically occurs via swabbing (or adhesive lift followed by swabbing of the adhesive) or submersion. Each of these methods have benefits and drawbacks. Results obtained through the swabbing technique have been extensively reported. However, swabbing generally results in lower overall DNA yields, especially compared to submersion. On the other hand, while submersion may increase DNA yields, extended incubation between buffer, shell casing and DNA may lead to additional oxidative damage of the DNA. Furthermore, submersion techniques risk the co-collection of gunpowder residue present within a spent shell casing, potentially introducing inhibitors into the sample.

SUMMARY OF THE DISCLOSURE

Non-destructive methods and devices are disclosed herein for overcoming the limitations associated with analyzing shell casings and other cylindrical items for biomolecular and fingerprint extraction and analysis. These methods and devices capitalize on the success of existing submersion-based protocols, while overcoming many of the challenges associated with those protocols.

In a preferred embodiment of these methodologies and devices, the open end of a spent shell casing (or like object) is plugged with a handle. This approach reduces the risk of sample contamination by gunpowder residue, while also providing a convenient means for handling the shell casing that reduces the risk of contamination or sample loss. Spin baskets (or extraction tubes) are provided which may be customized to different shell casing diameters, thereby substantially reducing the volume of extraction buffer required for sample collection and enable ease of centrifugation. A strong surfactant is preferably utilized during collection, which may reduce the amount of time needed for collection to just minutes. The surfactant is preferably of a type that draws on the extracellular nature of DNA in the sample in such a way as to almost instantaneously pull it into solution upon exposure to the buffer. The full buffer volume is then rapidly collected through the spin basket for DNA purification. Additionally, the use of magnetic beads to rapidly separate DNA from metal ions and other inhibitory agents is a primary advancement of the methods.

The systems and methodologies disclosed herein offer a possible paradigm shift for forensic laboratories as they analyze challenging types of casework evidence. In particular, these systems and methodologies may be utilized to improve the preservation, recovery and analysis of DNA, proteins, other forensically-relevant biomolecules, chemical, radiological, nuclear, or explosive residues, and fingerprints collected from shell casings or other like samples.

In one aspect, a method is provided herein for forensically processing a shell casing. The method comprises (a) providing a shell casing comprising a wall which has a first opening on a first end thereof and which encompasses an interior volume, wherein said shell casing has a forensic sample disposed thereon; (b) disposing a plug in said first opening, thereby obtaining a plugged shell casing; (c) inserting the plugged shell casing into a container having a liquid medium disposed therein which solubilizes at least a portion of said forensic sample, thereby obtaining a solubilized sample; and (d) subjecting the solubilized sample, or a product derived therefrom, to forensic analysis.

In another aspect, and in combination with a shell casing comprising a wall which has a first opening on a first end thereof and which encompasses an interior volume, a handling device is provided for handling said shell casing. The handling device comprises a plug which pressingly engages the interior surface of said shell casing; and a handle which extends from said plug.

DETAILED DESCRIPTION

Figure 1:
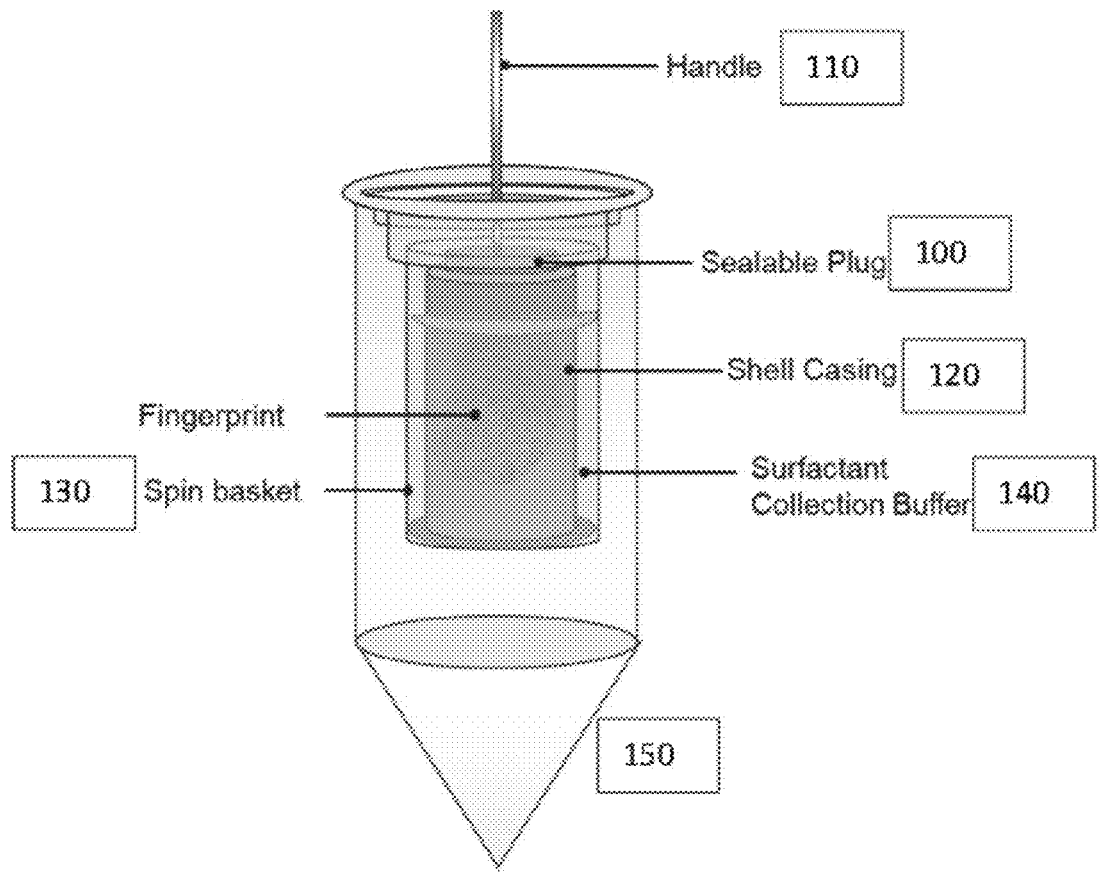
FIG. 1 is an illustration of an embodiment of a device and process for the recovery of biomolecules from shell casing evidentiary samples.

Methods and devices are disclosed herein for overcoming the limitations associated with methods of submerging shell casings for DNA extraction. Preferred embodiments of the methods and devices disclosed herein capitalize on the success of existing submersion-based protocols, while overcoming many of the challenges associated with those protocols.

In a preferred embodiment of these methodologies and devices, the open end of a spent shell casing is plugged with a handle. This approach reduces the risk of sample contamination by gunpowder from within the shell casing. It also provides a convenient means for handling the shell casing, while also reducing the risk of contamination or sample loss. Spin baskets are provided which may be customized to different shell casing diameters, thereby substantially reducing the volume of extraction buffer required for sample collection. A strong surfactant is preferably utilized during collection, which may reduce the amount of time needed for collection to just minutes. This surfactant is preferably selected to draw on the extracellular nature of DNA in the sample, which is almost instantaneously pulled into solution upon exposure to the buffer. The full buffer volume is then rapidly collected through the spin basket for DNA purification.

The systems and methodologies disclosed herein offer a possible paradigm shift for forensic laboratories as they analyze challenging types of casework evidence. In particular, these systems and methodologies may be utilized to improve the recovery and analysis of DNA, proteins, and other forensically-relevant biomolecules collected from bullet shell casing samples.

The devices and methodologies disclosed herein facilitate the handling of shell casings during forensic analysis through the use of a handle inserted into the shell casing. The handle is connected to a plug which seals the inside of the shell casing, thus preventing egress of the collection buffer into the interior of the casing. The shell casing is exposed to the collection buffer for a short time, further simplifying the process and reducing the risk of DNA degradation by copper or other metal ions also present in the sample. The recovery of DNA and other biomolecules may be maximized by keeping the collection buffer volume as low as possible. Recovery is further maximized via the use of a spin basket or similar collection tube that permits centrifugal separation of the collection liquid from the evidence. DNA and other biomolecules may then be rapidly extracted from the collection buffer, thus shortening the overall analysis time associated with processing shell casing evidence to a fraction of the time experienced with most current forensic protocols.

One skilled in the art will appreciate that the preferred embodiments of the devices and methodologies disclosed herein offer several advantages over many of the sample collection protocols currently utilized in the forensic arts. For example, the use of a sealable plug prevents the collection buffer from contacting gunpowder residue inside a spent shell casing. This prevents co-extraction of chemical compounds which may degrade DNA or inhibit analysis. The inclusion of a handle attached to the plug permits simplified manipulation of the shell casing to minimize the risk of contamination or sample loss due to handling of the casing. The use of custom-sized extraction tubes or spin baskets that are just larger than the diameter of each type of shell casing decrease the amount of collection buffer required to coat the entire surface of the shell casing, thereby reducing the effects of dilution of biomolecules collected from the surface. The incorporation of a strong surfactant collection buffer to rapidly solubilize and extract biomolecules from the surface of the shell casing reduces the amount of time that DNA and metal ions responsible for DNA degradation are together in solution. The use of custom sized extraction tubes or spin baskets enables rapid separation of the collection buffer from the shell casing via centrifugation. The use of magnetic beads allows for rapid separation of DNA from metal ions and other inhibitory agents. Taken together, these various advantages offer notable improvements over currently existing sample protocols. These advantages may advance the state-of-the-art in the analysis of bullet shell casing evidence across the spectrum of casework analysis, while also reducing reagent volumes, analysis time and skill-level requirements.

Figure 2:
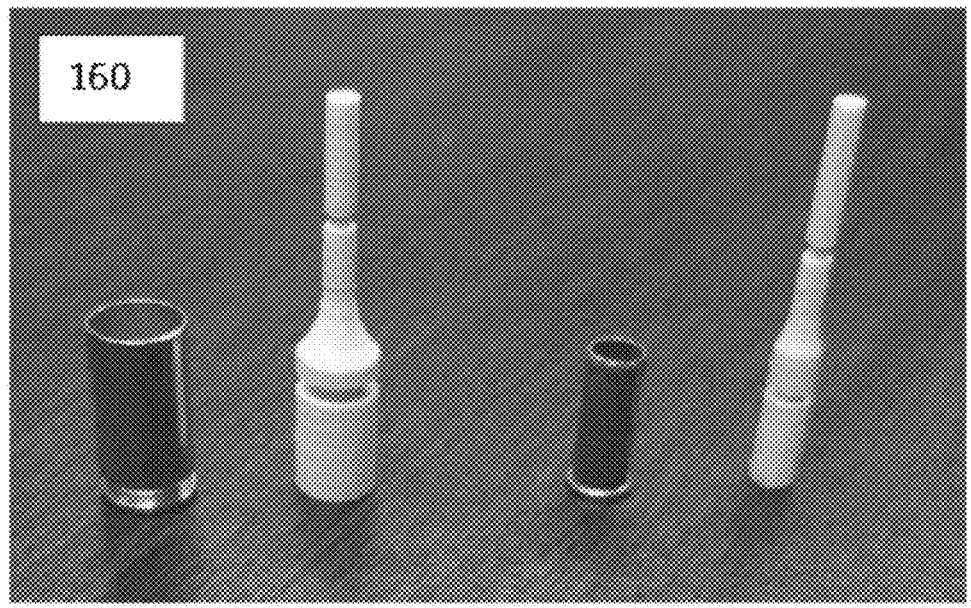
FIG. 2 depicts some particular, non-limiting embodiments of plugs and handles of the type disclosed herein for insertion into shell casings (shown prior to insertion into shell casings).
Figure 3:
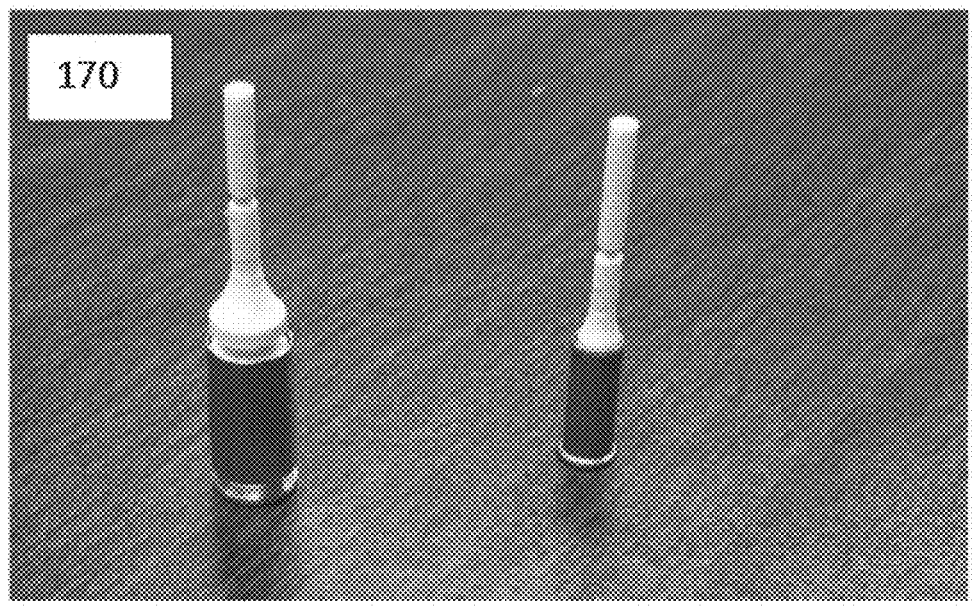
FIG. 3 depicts the plugs and handles of FIG. 2 following insertion into shell casings.

The devices and methodologies disclosed herein may be further understood with respect to the particular, non-limiting embodiments disclosed in FIGS. 1-3. With reference to FIG. 1, an embodiment of the technology disclosed herein for recovering biomolecules from shell casing evidentiary samples is depicted. In the particular embodiment depicted therein, a plug 100 is inserted into the shell casing 120 to prevent gunpowder residue from contacting the extraction buffer. The plug 100 is attached to a handle 110 to simplify handling. The shell casing 120 is inserted into a tube or spin basket device 130 containing a strong surfactant buffer 140, which acts to lift organic molecules from the surface of the shell casing 120. The sample is then centrifuged at high speed, separating the collection buffer from the shell casing 120 through a filter device and into a secondary collection tube 150.

The plugs 100 depicted are attached to handles 160 and may be custom-sized to different shell casing sizes. The plugs 100 contain a lower groove for a rubber O-ring to achieve a tight seal with the shell casing 120. The plugs 100 may then be inserted into shell casings 170 to form a tight seal that prevents gunpowder residue from contacting the collection buffer.

In a preferred embodiment of a methodology disclosed herein, spent brass shell casings are plugged with a custom 3D printed or injection molded insert which contains rubber O-rings to form a tight seal with the inner surface of the shell casing. This plug is attached to a plastic shaft that serves as a handle to aid in the manipulation of the shell casing. A custom-sized collection tube is selected, based on the diameter of the shell casing, such that the tube is just wide enough to permit insertion of the shell casing. A small amount of surfactant buffer (less than 500 µL) is added to the collection tube. The shell casing is gently inserted into the tube using the handle and rotated through the buffer. The collection tube is then capped, and the full liquid volume is collected into a secondary collection tube via centrifugation. DNA is then extracted from the collected buffer using an appropriate DNA purification kit such as Qiagen DNA Investigator. DNA eluted from the beads may be subjected to genetic analysis. Protein may also be separately eluted from the DNA purification spin column or affinity beads following DNA elution by the use of heat and a strong reducing agent. Eluted proteins may then be used for proteomic or proteogenomic analysis.

In some embodiments, the method used to plug the shell casing may include the use of a glue, epoxy, wax, or other solid capable of filling and sealing the inside of the shell casing from exposure to the collection buffer. In this case, a handle may be inserted into the plug material. In other embodiments, traditional DNA collection buffers, including those that contain metal chelators, may be used during the sample collection process.

In some embodiments, the shell casing may be removed from the collection buffer without the incorporation of a centrifugation step to recover the entirety of the collection buffer from the evidentiary surface. In other embodiments, other DNA extraction procedures may be utilized to purify recovered DNA for analysis, including commercial kits and organic extractions (e.g., phenol chloroform).

Example 1

The present example illustrates the assembly of a 0.22 caliber and 9 mm cartridge casings assembly.

A clean, dead air-box/working space was obtained by treatment with RNAse followed by 70% IPA. The 0.22 caliber and 9 mm shell casings were submerged in RNase Away® for 10 minutes to remove DNA and RNA signatures, followed by a quick rinse in water and 70% isopropanol to perform a low-level disinfection of microorganisms and to remove remaining residues, dirt, and gunpowder. Designated cleaning bins were provided for casings, separate from other surfaces and medias also being decontaminated.

After the casings were clean, they were transferred to a clean lab bench or dead box along with decontaminated materials (the decontaminated materials were wiped with RNAse followed by 70% IPA) required for epoxying. The following items were gathered for the subsequent steps:
(a) the 0.22 caliber and 9 mm spent casings;
(b) plastic straws/lollipop that are easily cut with scissors;
(c) casting compound Devcon's Flow-Mix® 5 Minute Epoxy;
(d) Devcon's 1:1 Mixing Nozzle; and
(e) a blunt head 8-gauge needle.

A plastic straw was positioned inside of each casing such that it touched the bottom of the casing. Two partitioned casting compounds were mixed in epoxy by attaching the 1:1 mixing nozzle to the end of the epoxy container along with the blunt head 8-gauge needle on top of the nozzle.

The blunt head needle was set into the casing. The mixed hardener and resin were then injected into the casing keeping consistent, gentle pressure on the epoxy plunger. The space around the straw was filled, taking care to surround the plastic straw as evenly as possible. Epoxy was added until the space around the straw was filled up and the surface level was even with the height of the casing. Any air bubbles that formed at the surface were popped with the needle and the resulting gap was filled in, if possible. After the epoxy was filled to the top of the casing, the epoxy was given time to set (~5 minutes) before the casing was moved. The epoxy-filled casings were then allowed to cure overnight before further processing. After all materials settled, the combined "lollipop" with the casing was sent back through the decontamination process.

Two labeled, clear, plastic bins were provided for the designated storage of casings with, respectively, artificial prints already applied, and decontaminated assembled casings ready to retain artificial/latent/cheater prints. The walls of these bins were lined with slit polyurethane foam. After decontamination, the now-handled casings were arranged in the slits of the foam to dry in the latter of the two bins.

If artificial prints are applied to the casings, those may be prepared in a separate decontaminated dead box or lab bench. If cheater or latent prints are being prepared, these prints may be applied to the surface of the casing. In the case that the thumb of the person applying a print is larger than the vertical length of the casing, the fingerprint may be applied laterally so that the thumb rolls along the curved surface of the casing and an entire print is applied.

After the artificial print mixture is prepared and the decontaminated casings are dry, the casings are transferred to a separate designated bin for artificial print casings in the same fashion as the decontaminated one. The handled casings are fit into the slits of the foam, taking care that each casing is easily accessible to pipette the artificial print mixture and is spaced far enough apart. Once all of the casings are in place, 5 µL of the artificial print mixture is spotted along each surface, taking care not get too close to the sides for it to roll off. The bin is then closed and the artificial prints are allowed to dry overnight before collection.

Example 2

This example illustrates print collection from 0.22 mm and 9 mm shell casings.

The now-dried casings are removed from the plastic bin they were stored in. For artificial prints, some oxidation may have occurred where the print was applied (represented with greenish discoloration of the surface).

A 285 µL aliquot of RapiGest is added to a Lyse& Spin column (for 0.22 caliber) or a suitable amount of RapiGest to a 5 mL gravity column for larger casings (9 mm). Using the handle, the shell casing is lowered into the column and submerged in the buffer. The column is tipped at a 45° angle, and the casing is slowly rotated in the RapiGest buffer for 1 minute at room temperature. Care is taken to ensure that the buffer coats the full surface area of the shell casing as it is rotated through the liquid. The handle is broken off (if necessary) and the tube is capped and centrifuged at maximum speed for 1 minute to recover the RapiGest solution into a collection tube.

Example 3

This example illustrates SP3 stratification.

The entire recovered sample volume is transferred into a new microcentrifuge tube. A ThermoMixer is preheated to 60° C. The sample tube is heated in a ThermoMixer at 60° C. for 30 min with mixing at 1,000 r.p.m., after which the tube is removed from the ThermoMixer and allowed to cool to room temperature in a rack on the lab bench.

The Thermomixer is set to 24° C., and 180 µL of AMPure XP beads that have been equilibrated to room temperature are added to the samples. The resulting mixture is pipetted ten times to ensure good mixing and homogeneity.

The beads are warmed at room temperature for at least 30 minutes prior to use, and care is taken to ensure complete homogenization of the SP3 beads in solution.

In order to induce binding of the proteins to the beads, 100% ethanol is added in equal volume. The tube is briefly shaken to ensure homogeneity. Excessive shaking of the mixture is avoided after the addition of ethanol, in order to minimize losses due to beads sticking to the upper regions of the tube. Care is also taken to avoid flicking the tube to mix it.

The binding mixture is incubated in a ThermoMixer at 24° C. for 5 min at 1,000 rpm. After the binding is complete, the tube is placed in a magnetic rack and incubated it until the beads have migrated to the tube wall. The unbound supernatant is removed and discarded.

The tube is removed from the magnetic rack, and 180 µL of 80% ethanol SP3 rinse solution is added. The resulting mixture is pipette-mixed to reconstitute and rinse the beads.

Care is taken to avoid being overly aggressive during pipette mixing and rinsing of the SP3 beads, since aggressive pipette mixing may result in protein loss. Typically, pipetting using a 200-µL tip, three to four times until the beads are reconstituted, is enough. The tube is placed on the magnetic rack and incubated until the beads have migrated to the tube wall.

The supernatant is then removed, taking care to not disrupt the beads. The 80% ethanol wash steps are repeated two further times to completely rinse the proteins bound to the SP3 beads.

After removal of the final 80% ethanol rinse, care is taken to extract as much of the residual rinse liquid (<5 µL is optimal) as possible. It is not necessary to completely air-dry the SP3 beads. A quick spin after removal of final ethanol rinse can help with excess liquid stuck up in the tube.

The sample is then removed from the magnetic rack, and 30 µL of DNA elution buffer (TE) is added to the reaction tube. The beads are gently resuspended by pipetting, and are incubated at room temperature for 2 minutes.

The reaction tube is placed onto the Magnetic Separation Rack for 1 minute to separate beads from the solution. The eluted DNA is aspirated and transferred into a clean tube, taking care not to pipette up any beads. If beads are accidently carried over, the DNA sample is placed back on the rack, allowing the beads to separate, and the eluate is transferred into a clean tube. This process is repeated, if necessary, until no beads are present.

The DNA concentration of the DNA fraction is measured using a Qubit 1× dsDNA High Sensitivity assay, per the manufacturer's instructions. DNA may be stored short term (up to 1 week) at 2-8° C., or may be immediately frozen and stored long term at or below −15° C. Then, 50 μL 1× S-Trap Lysis Buffer+100 mM DTT is added to the remaining beads, and they are gently resuspended. The sample is boiled for 5 minutes, and subjected to a brief spin.

The reaction tube is placed onto the Magnetic Separation Rack for 1 minute to separate beads from the solution. The eluted protein is aspirated and transferred into a clean tube, taking care not to pipette up any beads. If any beads are accidently carried over, the protein sample is placed back on the rack, the beads are allowed to separate, and the eluate is transferred into a clean tube. This process is repeated as necessary until no beads are present.

A second 50 μL 1× S-Trap Lysis Buffer+100 mM DTT is added to the remaining beads, and the boiling and recovery steps are repeated. The recovered supernatant is pooled, which typically yields ~100 μL total volume. Any remaining elution buffer is saved as a negative control comparator for Qubit.

The protein concentration of the sample is measured using a Qubit Protein Assay Kit and the corresponding Protein program on the Qubit instrument. The sample is then subjected to gel analysis and/or S-Trap protein digestion SOP, starting at the protein reduction and alkylation step.

Various forensic samples may be utilized in, or may be the subject of, the methodologies and devices disclosed herein. These include, without limitation, fingerprints, DNA, RNA, proteins, toxins, pathogens, biological agents, explosives, pharmaceutical compounds, drugs, chemical agents, compounds and molecules.

The above description of the present invention is illustrative, and is not intended to be limiting. It will thus be appreciated that various additions, substitutions and modifications may be made to the above described embodiments without departing from the scope of the present invention.

What is claimed is:

1. A method for forensically processing a shell casing, comprising:
   providing a shell casing comprising a wall which has a first opening on a first end thereof and which encompasses an interior volume, wherein said shell casing has a forensic sample disposed thereon;
   disposing a plug in said first opening, thereby obtaining a plugged shell casing;
   inserting the plugged shell casing into a container having a liquid medium disposed therein which solubilizes at least a portion of said forensic sample, thereby obtaining a solubilized sample; and
   subjecting the solubilized sample, or a product derived therefrom, to forensic analysis.

2. The method of claim 1, wherein said shell casing is a spent shell casing.

3. The method of claim 1, wherein said plug seals said first opening.

4. The method of claim 1, wherein said wall has an interior surface, and wherein said plug pressingly engages the interior surface of said shell casing.

5. The method of claim 4, wherein said wall has an exterior surface, and wherein said forensic sample is disposed on said exterior surface.

6. The method of claim 1, wherein said container is a spin basket.

7. The method of claim 1, wherein said liquid medium is a collection buffer.

8. The method of claim 1, wherein said liquid medium is a DNA collection buffer containing a chelator.

9. The method of claim 1, further comprising a handle attached to said plug, wherein the plug is inserted into the shell casing such that the handle extends from said shell casing.

10. The method of claim 1, further comprising:
    separating the liquid medium from the shell casing through the use of a centrifuge.

11. The method of claim 1, wherein said plug is equipped with a peripheral groove having an O-ring seated therein.

12. The method of claim 1, wherein said forensic sample includes DNA.

13. The method of claim 1, wherein said forensic sample includes RNA.

14. The method of claim 1, wherein said forensic sample includes a protein.

15. The method of claim 1, wherein said forensic sample is a fingerprint.

16. The method of claim 1, wherein said forensic sample is selected from the group consisting of pathogens, toxins and biological agents.

17. The method of claim 1, wherein said forensic sample is a chemical compound.

18. The method of claim 1, wherein disposing a plug in said first opening includes: placing a curable liquid in the first opening; and
    curing the curable liquid.

19. The method of claim 18, further comprising:
    placing a handle in the curable liquid prior to curing the liquid.

20. The method of claim 1, wherein disposing a plug in said first opening includes: placing a molten material in the first opening; and
    solidifying the molten material.

21. The method of claim 20, further comprising:
    placing a handle in the molten material prior to solidifying the molten material.

22. The method of claim 1, wherein the forensic sample contains at least one protein, and further comprising:
    mixing the solubilized sample with a plurality of beads that bind to said at least one protein, thereby producing loaded beads; and
    isolating the loaded beads from the liquid medium.

23. The method of claim 22, further comprising:
    stripping the at least one protein from the loaded beads, thereby obtaining a protein solution; and
    subjecting the protein solution to forensic analysis.

* * * * *